(12) United States Patent
Pasquali et al.

(10) Patent No.: US 9,393,202 B2
(45) Date of Patent: Jul. 19, 2016

US009393202B2

(54) PARTICLE SIZE REDUCTION OF AN ANTIMUSCARINIC COMPOUND

(71) Applicant: CHIESI FARMACEUTICI S.p.A., Parma (IT)

(72) Inventors: Irene Pasquali, Parma (IT); Andrea Casazza, Parma (IT); Elena Losi, Parma (IT); Mark Saunders, Hertfordshire (GB)

(73) Assignee: CHIESI FARMACEUTICI S.p.A, Parma (IT)

( * ) Notice: Subject to any disclaimer, the term of this patent is extended or adjusted under 35 U.S.C. 154(b) by 95 days.

(21) Appl. No.: 14/258,147

(22) Filed: Apr. 22, 2014

(65) Prior Publication Data

US 2014/0322142 A1    Oct. 30, 2014

(30) Foreign Application Priority Data

Apr. 26, 2013 (EP) .................................. 13165483

(51) Int. Cl.
- *A61K 9/16* (2006.01)
- *A61K 31/40* (2006.01)
- *A61K 9/00* (2006.01)
- *A61K 9/14* (2006.01)

(52) U.S. Cl.
CPC ............. *A61K 9/1688* (2013.01); *A61K 9/0075* (2013.01); *A61K 9/14* (2013.01); *A61K 31/40* (2013.01)

(58) Field of Classification Search
None
See application file for complete search history.

(56) References Cited

U.S. PATENT DOCUMENTS

2010/0266696 A1* 10/2010 Muhrer ................ A61K 9/0075
424/489

FOREIGN PATENT DOCUMENTS

| WO | 01/76575 | 10/2001 | |
| WO | 2008/000482 | 1/2008 | |
| WO | WO 2008000482 A1 * | 1/2008 | ........... A61K 9/0075 |
| WO | 2009/074662 | 6/2009 | |
| WO | 2009/074666 | 6/2009 | |

OTHER PUBLICATIONS

U.S. Appl. No. 14/327,920, filed Jul. 10, 2014, Pasquali et al.
European Search Report in Application No. 13165483.2 issued Sep. 30, 2013.
P. Bowen, "Journal of Dispersion Science and Technology", vol. 23, No. 5 (2002) pp. 631-662.

* cited by examiner

*Primary Examiner* — Carlos Azpuru
*Assistant Examiner* — Casey Hagopian
(74) *Attorney, Agent, or Firm* — Oblon, McClelland, Maier & Neustadt, L.L.P

(57) ABSTRACT

A stable crystalline micronized particulate of a glycopyrronium salt may be prepared by suspending the drug in a water-immiscible anti-solvent in which the drug has little or no solubility and micronizing the suspension. The resulting drug particles are physically stable with regard to agglomeration and/or aggregation on storage.

12 Claims, No Drawings

PARTICLE SIZE REDUCTION OF AN ANTIMUSCARINIC COMPOUND

CROSS REFERENCES TO RELATED APPLICATIONS

This application claims priority to European Patent Application No. 13165483.2 filed on Apr. 26, 2013, which is incorporated herein by reference in its entirety.

BACKGROUND OF THE INVENTION

1. Field of the Invention

The present invention relates to processes for preparing micronized particles of an anti-muscarinic drug. The present invention also relates to pharmaceutical formulations, preferably dry powder formulations for the prevention and/or treatment of respiratory diseases, which contain such micronized particles, and to methods for the prevention and/or treatment of respiratory diseases.

2. Discussion of the Background

It is known that water soluble quaternary ammonium compounds with antimuscarinic activity tend to irreversibly agglomerate during storage. This is attributed to the formation of crystal bridges between neighbouring particulates due to the absorption of moisture post micronization and subsequent recrystallisation of surface amorphous content which is generated by the high energy micronization process. This problem affects the physical and chemical stability of the drug and its subsequent performance in formulations.

Glycopyrronium is an anti-muscarinic drug commercially available as the bromide salt since many years. Glycopyrronium bromide has two chiral centers corresponding to four isomeric forms comprising 2 pairs of diastereoisomers, namely (3S,2'R)-, (3R,2'S)-, (3R,2'R)-, and (3S,2'S)-[(cyclopentyl-hydroxyphenylacetyl)oxy]-1,1-dimethylpyrrolidinium bromide. Commercially available glycopyrronium bromide consists of the purified "threo" diastereoisomer (3R, 2'S) and (3S,2'R) and is hereinafter indicated as rac-glycopyrronium bromide.

However, as other anti-muscarinic agents, glycopyrronium salts have significant stability problems, especially immediately following conventional micronization process by milling.

In fact, glycopyrronium bromide, once micronized, has a strong tendency to irreversibly aggregate and/or agglomerate, which severely hinders downstream drug processing, particularly the preparation of dry powder formulations for administration by inhalation capable of delivering a good respirable fraction.

Various processes have been proposed to process drugs to alter certain physicochemical properties of the drug. However many of those processes involve the use of solvents that have low pharmacological tolerability and therefore their residual presence needs to be strictly monitored. In addition, many of these solvents are highly flammable, making larger scale commercial manufacture difficult. Other known solvent treatment processes, including those using polar solvents, water, or water vapor, tend to cause local solvation processes to occur that subsequently leads to particle growth or irreversible aggregation and agglomeration during drying or storage.

In addition, it is well known that the current state-of-the-art high energy physical processing procedures, such as air jet milling, dry powder ball-milling or high pressure homogenization, result in a partial loss of drug crystallinity. These micronized materials are often subjected to post micronization conditioning; for example, storage under elevated temperature and/or relative humidity in order to condition out any process induced structural disorder and/or amorphous content.

For example, WO 2009/074662, which is incorporated herein by reference in its entirety, discloses the conditioning the post micronized material, such as a glycopyrronium salt, under elevated temperatures (>40° C.) and dry conditions for varying periods of time in order to condition/recrystallize the process induced structural disorder and amorphous content and prevent further irreversible agglomeration occurring on storage. However, exposing the afore-mentioned material to conditions of elevated relative humidity post micronization results in the rapid formation of crystal bridges and irreversible particle agglomeration/crystal growth and therefore this post-micronization elevated temperature conditioning is critical to maintaining a stable product.

Analogously, WO 2009/074666, which is incorporated herein by reference in its entirety, discloses a method for making micronized active particles of water soluble drugs such as a glycopyrronium salt for use in a pharmaceutical composition for pulmonary inhalation that involves high pressure homogenization of said particles in a polar anti-solvent, for instance acetone, ethanol or propan-1-ol, to achieve particle size reduction and subsequent conditioning of the micronized material under dry elevated temperatures to achieve a physically stable powder with respect to agglomeration/aggregation or particle growth.

WO 2005/025536, which is incorporated herein by reference in its entirety, discloses a method for making composite active particles for use in a pharmaceutical composition for pulmonary inhalation that involves jet milling active particles with certain additive materials to maintain stability and enhance fine particle fraction and fine particle dose. Glycopyrronium is cited among other active ingredients. It is anyway difficult and time consuming to eliminate said additives if not needed.

In view of these considerations, it would be highly advantageous to provide a process for preparing micronized particles of a glycopyrronium salt, that are physically stable and do not need further treatments for avoiding the formation of agglomerates. The problem is solved by the process of the present invention.

SUMMARY OF THE INVENTION

Accordingly, it is one object of the present invention to provide novel processes for preparing micronized particles of an anti-muscarinic drug.

It is another object of the present invention to provide novel processes for preparing micronized particles of a pharmaceutically acceptable salt of glycopyrronium.

It is another object of the present invention to provide novel pharmaceutical formulations, which contain such micronized particles.

It is another object of the present invention to provide novel dry powder formulations for the prevention and/or treatment of respiratory diseases, which contain such micronized particles.

It is another object of the present invention to provide novel methods for the prevention and/or treatment of respiratory diseases by administering to a subject in need thereof an effective amount of such micronized particles or of such a formulation.

These and other objects, which will become apparent during the following detailed description, have been achieved by the inventors' discovery that micronized particles prepared by the following process exhibit improved properties.

Thus, in a first aspect the present invention provides a process for the preparation of micronized particles of a pharmaceutically acceptable salt of glycopyrronium, the process comprising the steps of:

feeding the micronization chamber of a wet milling apparatus, optionally containing grinding media, with a water immiscible hydrocarbon or derivative thereof which is liquid at room temperature and pressure, also having a dielectric constant lower than 15 and a density of 1.3 to 2 g/cm$^3$ (the anti-solvent);

suspending the particles of the glycopyrronium salt in said anti-solvent;

micronizing said suspended particles at a pressure of equal or lower than 200 kPa;

optionally, drying the obtained micronized particles; whereby at least 90% of said particles have a diameter of less than 10 micron.

The process of the present invention may be carried out in the absence of any additive acting as stabilizing agent.

In a second aspect, the present invention provides a process for preparing a formulation for inhalation comprising the step of mixing the above micronized particles with one or more propellants or carriers.

In a third aspect, the present invention provides physically stable micronized crystalline particles of a pharmaceutically acceptable salt of glycopyrronium having a cohesive-adhesive balance (CAB) value of 0.5-1.5 obtainable by the aforementioned process.

In a fourth aspect, the present invention provides formulations for inhalation comprising the afore-mentioned micronized particles.

In a fifth aspect, the present invention provides inhalers filled with such a formulation.

In a sixth aspect, the present invention provides methods for the prevention and/or treatment of respiratory diseases by administering to a subject in need thereof an effective amount of such micronized particles or of such a formulation.

DETAILED DESCRIPTION OF THE PREFERRED EMBODIMENTS

The term "micronization" refers to the process of reducing the average diameter of a solid material's particles. Usually, the term micronization is used when the particles that are produced are only a few micrometres in diameter. Traditional micronization techniques are based on the use of friction to reduce particle size. Such methods include milling and grinding. Reduction in particle size may also take place as a result of collision and impact.

The term "aggregate" means to assemble or combine together. Freshly micronized drugs tend to take the form of a fine powder that tends to spontaneously coalesce over time to form aggregates of the drug. These aggregates resemble a less fine or even coarse powder.

The term "agglomerate" means to form into a mass or cluster, particularly in the presence of moisture. Agglomerates of micronized drugs tend on storage, particularly in the presence of moisture, to form a coarse powder, clumps or even a substantially singular mass of drug.

The presence of agglomerates of the drug in the formulation may be detected by a Near Infrared Spectrophotometer provided with a microscope according to methods known to the skilled person.

The term "physically stable" means that, on storage, there is no evidence of particle growth or agglomeration of the drug particles. There should not be an increase in the particle size which 95% of the particles in the drug product have a diameter of less than, as measured by the cumulative distribution to impact on the inhalatory performances. The cumulative distribution of a particulate product gives an indication of the amount of different particle sizes within a sample. The cumulative distribution of a sample may be measured using any suitable apparatus. One particular apparatus that can be used is the Sympatec Dry Dispersion Size Analyser.

The term "chemically stable" refers to a drug that, upon storage, meets the requirements of the EMEA Guideline CPMP/QWP/122/02 referring to "Stability Testing of Existing Active Substances and Related Finished Products".

The term "anti-solvent" means a liquid having little or no solvation capacity for the drug. The solubility of the drug in the anti-solvent should be less than about 1 mg/ml determined according to methods known to the skilled person. Preferably, the solubility of the drug should be less than about 100 μg/ml. More preferably, the solubility of the drug should be less than about 10 μg/ml.

In the context of the present invention, the term "water immiscible" means that less than 100 ppm, and preferably less than 10 ppm of water can dissolve in the anti-solvent. The amount of residual water can be determined according to methods known to the skilled person, such as Karl-Fisher.

The term "conditioning" means an exposure of the powder placed in a suitable container to a combination of temperature and relative humidity conditions kept under control.

The term "stabilizing agent" refers to agents which are used to stabilize a drug in order to reduce or prevent the drug from agglomerating or aggregating. A stabilizing agent generally reduces the cohesion between particles and prevents fine particles becoming attached to each other. Stabilizing agents include metal stearates such as magnesium stearate and calcium stearate, ionic and non-ionic surfactants, and polymers such as cellulose ethers, PVP or PVA.

The "particle size" is the Gaussian distribution of the diameter of particles.

Said particle size can be quantified by measuring the volume diameter by laser diffraction using suitable known instruments such as, for instance, the Malvern apparatus.

The volume diameter (VD) is related to the mass diameter (MD) by the density of the particles (assuming a size independent density for the particles).

In the present application, the particle size is expressed in terms of volume diameter, and the particle size distribution is expressed in terms of d(v0.5), which corresponds to the diameter of 50 percent by volume of the particles and, also in terms of d(v0.9) and d(v0.1) which express the values under which 90% of particles and 10% of the particles of a sample have a lower volume diameter, respectively.

Upon aerosolization, the particle size is expressed as mass aerodynamic diameter (MAD) and the particle size distribution as mass median aerodynamic diameter (MMAD). The MAD indicates the capability of the particles of being transported suspended in an air stream. The MMAD corresponds to the mass aerodynamic diameter of 50 percent by weight of the particles.

The term "good flowability" refers to a formulation that is easy handled during the manufacturing process and is able to ensure an accurate and reproducible delivering of the therapeutically effective dose.

Flow characteristics can be evaluated by different tests such as angle of repose, Can's index, Hausner ratio or flow rate through an orifice.

The term "good homogeneity" refers to a formulation wherein, upon mixing, the uniformity of distribution of the active ingredient, expressed as the coefficient of variation (CV) also known as relative standard deviation (RSD), is equal to or less than 5.0%.

The term "respirable fraction" refers to an index of the percentage of active particles which would reach the deep lungs in a patient.

The respirable fraction, also termed fine particle fraction, is evaluated using suitable in vitro apparata such as Multistage Cascade Impactor, Multi Stage Liquid Impinger (MLSI) or Next Generation Impactor (NGI) according to procedures reported in common Pharmacopoeias.

The respirable fraction, also termed fine particle fraction (FPF), is evaluated using a suitable in vitro apparatus such as Andersen Cascade Impactor (ACI), Multi Stage Liquid Impinger (MLSI) or Next Generation Impactor (NGI), preferably by ACI, according to procedures reported in common Pharmacopoeias, in particular in the European Pharmacopeia (Eur. Ph.) 7.3, 7$^{th}$ Edition, which is incorporated herein by reference in its entrety. It is calculated by the percentage ratio between the fine particle mass (formerly fine particle dose) and the delivered dose.

The delivered dose is calculated from the cumulative deposition in the apparatus, while the fine particle mass is calculated from the deposition of particles having a diameter <5.0 micron.

In the context of the present invention, the pressure values are expressed in kiloPascal (kPa) which correspond to 1000 pascal (Pa). Other units are admitted such as bar ($10^5$ Pa), mmHg, mmH$_2$O, and atm.

The present invention is directed to a process for the preparation of micronized particles of a pharmaceutically acceptable salt of glycopyrronium. It has been found that, by operating according to the conditions disclosed hereinafter, a physically stable powder is obtained that avoids all the usual post micronization physicochemical issues that make conventional formulation processing difficult, especially in the production of dry powder formulations for administration by inhalation.

In particular it has been found that the drug particles which result from the process of the invention are stable such that they are aggregation and/or agglomeration resistant. In other words, the tendency of the resulting dry micronized material to aggregate and/or agglomerate post processing is minimized or completely avoided.

Said drug particles also show good flow properties. Moreover, the drug particles are substantially free of amorphous content.

More surprisingly this is obtained without adding further stabilizing agents and without resorting to tedious and time consuming post micronization conditioning steps at elevated temperatures.

Even more surprisingly, it has been found that, by operating according to the conditions of the process of the invention, a uniform suspension is obtained without the use of any excipients such as the aforementioned stabilizing agents. Therefore, micronization of the drug is carried out in the absence of any further excipients. This makes the process of the invention much simpler to carry out.

Advantageously any organic or inorganic pharmaceutically acceptable salt of glycopyrronium may be used. Organic salts may comprise, for instance, formate, acetate, trifluoroacetate, propionate, butyrate, lactate, citrate, tartrate, malate, maleate, succinate, methanesulfonate, benzenesulfonate, and benzoate, while inorganic salts may include, but are not limited to, fluoride, chloride, bromide, iodide, phosphate, nitrate, and sulfate.

Preferably, an inorganic salt is used selected from the group consisting of fluoride, chloride, bromide, and iodide, preferably chloride or bromide, even more preferably bromide.

Glycopyrronium may be used in the form of any of the pure enantiomers or diastereoisomers or any combination thereof in practicing the present invention. In a preferred embodiment, the (3S,2'R), (3R,2'S)-3-[(cyclopentylhydroxyphenylacetyl)oxy]-1,1-dimethylpyrrolidinium bromide racemic mixture is used, also known as rac-glycopyrronium bromide.

Preferably, micronization should take place in the absence of water. The anti-solvent should be hence water immiscible and should contain no dissolved water.

Advantageously, the water immiscible anti-solvent may be a hydrocarbon or derivative thereof which is liquid at room temperature and pressure (about 20° C. and about 1 atm), also having a dielectric constant lower than 15 and a density of 1.3 to 2 g/cm$^3$. In a preferred embodiment of the invention, the density is comprised between 1.4 and 2 g/cm$^3$. A person skilled in the art would readily be able to determine the dielectric constant and the density of the anti-solvent, according to known methods.

In fact, it has been surprisingly found that if anti-solvents previously employed in particle size reduction by high pressure homogenization not fulfilling the above characteristics are used, for example acetone, ethanol or propan-1-ol, irreversible particle agglomeration during drying at low temperature is observed.

In some embodiments, the anti-solvent is an n-alkane or a haloalkane which is liquid at room temperature and pressure. Suitable alkanes range from n-pentane ($C_5H_{12}$) to n-$C_{17}H_{36}$ which are all liquid at room temperature and pressure. Preferred alkanes include n-pentane, n-hexane, n-heptane, n-octane, n-nonane, and n-decane. In some embodiments, the n-alkane may be n-pentane, n-hexane, n-heptane, or n-octane. In a particular embodiment, the alkane is n-heptane.

A suitable haloalkane is dichloromethane.

In other embodiments, the anti-solvent is a fluoroalkane or a hydrofluoroalkane. Suitable fluoroalkanes and hydrofluoroalkanes include perfluoropentane, perfluorohexane, perfluoroheptane, perfluorooctane, perfluorononane, perfluorodecane, and any mixture of isomers thereof as well as any hydrogen substituted derivative thereof such as 2H,3H-decafluoropentane.

In a particularly preferred embodiment of the present invention, the anti-solvent is selected from the group of perfluoroheptane or any mixture of isomers thereof perfluorodecane and decafluoropentane.

According to step (ii), the particles of the glycopyrronium salt are suspended in a water immiscible anti-solvent to give a suspension.

Said particles may be in a coarse particulate form or, alternatively they may have a pre-reduced particle size. Advantageously, said particles shall be nominally crystalline such that the atoms or molecules are arranged in a regular, periodic manner. However, the crystalline drug may contain some amorphous regions. Preferably, the drug should have a crystallinity equal to or higher than 90% or, more preferably, higher than 95%, more preferably higher than 98% as determined according to methods known to the skilled person.

The drug may be suspended in the chosen anti-solvent at a drug/anti-solvent ratio of between 1:200 w/v and 200:1 w/v. Preferably, the drug/anti-solvent ratio is between 1:1 w/v and 200:1 w/v, more preferably between 50:1 w/v and 150:1 w/v. In a preferred embodiment, the drug/anti-solvent ratio may be 100:1 w/v.

This suspension is then treated to reduce the particle size of the drug. Stabilizing agents or any other excipients need not be added to the suspension as these are not required in order to obtain a stable product.

Therefore, in particular embodiments, a suspension consisting essentially of the glycopyrronium salt suspended in the water immiscible anti-solvent is micronized. This allows the production of a pure drug product which is free from other substances.

Micronizing equipment is well known in the art and includes a variety of grinding and milling machinery. For example, suitable milling machinery for use in wet milling using an anti-solvent includes impact mills such as ball mills and planetary mills. Advantageously, the micronizing equipment is provided with a rotor or disc operating at a suitable speed.

In a preferred embodiment, the glycopyrronium salt is wet ball milled using a Planetary Mill PULVERISETTE (Fritsch, Germany) or a DM100 micro mill (Dena Technology Ltd, UK). Other suitable micronizing apparatus includes horizontal bead mills, for instance DYNO®-MILL (Glen Mills Inc, NJ); rotor-stator homogenisers, for instance Polytron (Glen Mills Inc, NJ), or available from Silverson, Australia and Heidolph Instruments, Germany; other apparatus that could suitably be used are annular gap bead mills, for instance Stirrer Bead CoBall®-Mill, type MS (FrymaKoruma, Germany).

In a preferred embodiment, the glycopyrronium salt is treated in the milling apparatus disclosed in WO 2007/020407, which is incorporated herein by reference in its entirety.

Said milling apparatus comprises a radially symmetrical sleeve having an axial passageway with an upstream inlet and a downstream outlet or vice versa, a radially symmetrical rotor located within the sleeve, one of the rotor and sleeve being rotatable relative to the other, the diameter of the rotor being less than the diameter of the sleeve at each axial position to define an annular passageway between the rotor and sleeve, one or both of the surfaces of the rotor and sleeve having formations adapted to increase the surface area encountered by particles in a fluid flow from the inlet to the outlet.

Advantageously in said apparatus, the particles of the glycopyrronium salt are re-circulated through reduction chamber for 2 to 10 cycles of treatment.

In micronization, some techniques involve the use of grinding or milling media to help to reduce the particle size of the drug. In the process of the present invention, such media of the same or different size are used and are present in the drug suspension whilst micronization is taking place.

The grinding media may be selected from grinding or milling beads formed of a material selected from the group consisting of polystyrene, polymethyl methacrylate (PMMA), polyamide, polycarbonate, polyurethane, Soda Lime Glass, steatite, ZirTA-NOR (Zirconia Toughened Alumina), zirconia silicate, zirconia silica, high density zirconia silica, toughened zirconia silica, magnesium stabilized zirconia oxide, cerium stabilized zirconia oxide, Yttrium stabilized zirconia oxide, tungsten carbide, silicon nitride or silicon carbide. In some embodiments, the grinding media are zirconium oxide milling beads. For processing, the diameter of the grinding media particles should be less than 25 mm, more preferably less that 10 mm, ideally less than 5 mm.

The micronization step should take place at a pressure equal to or lower than 200 kPa.

Some micronization techniques use high pressure in order to reduce the size of the drug particles. For example, pressures of between 500 bar and 2000 bar are commonly used in homogenisers. Surprisingly, it has been found that it is not necessary to use elevated pressure in the present invention. Preferably, the micronization of the drug is carried out at a pressure of 50 kPa to about 200 kPa. More preferably, a pressure of 50 kPa to 150 kPa is used. Even more preferably, the micronization of the drug is carried out at a pressure of 80 kPa to 120 kPa.

Suitable conditions for micronizing the suspension will vary with the apparatus and the processing anti-solvent. In general, when an apparatus provided with a disc/rotor is used, the speed of the disc/rotor at which the suspension is micronized may be from about 50 to about 500 rpm, preferably from about 100 to about 400 rpm, more preferably from about 150 to about 300 rpm. When the anti-solvent is 2H,3H-decafluoropentane, the disc/rotor speed at which the suspension is treated could be from 100 to 300 rpm. Suitable temperatures for homogenizing the suspension will vary with the drug and the anti-solvent concerned. In general, the temperature at which the suspension is homogenized is below the boiling point of the anti-solvent. Advantageously, the micronization step is performed at a temperature of from about 0° C. to 40° C., more advantageously from 5° C. to about 35° C. Preferably, the suspended drug is micronized at a temperature of from 10° C. to 30° C. and, more preferably from 10° C. to 25° C.

In a particular embodiment, the micronization step is carried out at ambient temperature (20±2° C.).

Suitable times for micronizing the suspended drug particles will vary with the anti-solvent and the grinding media concerned. In general, the suspended drug particles are treated for 1 to 300 minutes, preferably 15 to 240 minutes, more preferably 15 to 90 minutes. When the anti-solvent is 2H,3H-decafluoropentane and the grinding media is zirconium oxide balls of a 1 mm diameter, the suspension is treated at a speed of 200 rpm preferably for 30 to 90 minutes, more preferably for 60 minutes.

In some embodiments, a first anti-solvent may be used in the micronization process and a second anti-solvent may be optionally used to wash the micronized drug particles. In this regard, the process may further comprise a washing step in which a second anti-solvent is used to wash the micronized drug particles. Preferably, the second anti-solvent used in the washing step has a relatively high vapor pressure such that it can be removed during drying at a relatively low temperature, e.g., below 35° C. In other words, the second anti-solvent should be relatively volatile such that it can be removed during drying at a relatively low temperature (e.g, below 35° C.).

Advantageously, the vapor pressure of the second anti-solvent is higher than 5 kPa. More advantageously, the vapor pressure of the second anti-solvent is higher than 10 kPa. Preferably, the vapor pressure of the second anti-solvent is higher than 20 kPa. More preferably, the vapor pressure of the second anti-solvent is higher than 30 kPa. Even more preferably, the vapor pressure of the second anti-solvent is higher than 40 kPa. In certain embodiments, the vapor pressure of the second anti-solvent may be higher than 50 kPa. In other embodiments, the vapor pressure of the second anti-solvent may be higher than 60 kPa, preferably higher than 70 kPa. These vapor pressures are measured at 20° C. at 1 atm according to methods known to the skilled person.

In some embodiments, the second anti-solvent has a boiling point lower than 100° C. Advantageously, the anti-solvent has a boiling point lower than 90° C. More advantageously, the second anti-solvent has a boiling point lower than 80° C. Preferably, the second anti-solvent has a boiling point lower than 70° C. More preferably, the second anti-solvent has a boiling point lower than 60° C. Even more preferably, the second anti-solvent has a boiling point lower 50° C. In certain embodiments, the second anti-solvent has a boiling point lower than 40° C., preferably lower than 35° C., more preferably lower than 30° C.

These boiling points are determined according to methods known to the skilled person.

Having a relatively high vapor pressure and/or low boiling point allows the drug particles to be dried at a relatively low temperature (e.g., below 35° C.). Particular anti-solvents which are preferred for the washing step are decafluoropentane and pentane.

Instead of using a second anti-solvent to wash the micronized drug particles, the first anti-solvent in which the water soluble drug is micronized may have the properties described above for the second anti-solvent. Therefore, in some embodiments, the first anti-solvent may have a relatively high vapor pressure such that it can be removed during drying at a relatively low temperature (e.g., below 35° C.). Preferred vapor pressures are as above for the second anti-solvent. Further, the first anti-solvent may have a relatively low boiling point, for example, below 100° C. Preferred boiling points are as above for the second anti-solvent.

The process preferably involves a step of drying the micronized drug particles to remove any residual anti-solvent. Preferably, the drug particles are dried under a temperature of less than 40° C., preferably less than 35° C., more preferably less than 30° C., and even more preferably less than 25° C., to remove any residual anti-solvent. This can be achieved using any drying process known in the art such as vacuum drying, spray drying or supercritical fluid drying. Preferably the drug particles are spray-dried or vacuum dried.

The dried drug particles are preferably sieved, for example, through a 100 μm mesh sieve, to separate any residual grinding media and the resulting fine powder drug material collected.

In particular embodiments, if the anti-solvent is suitable for pharmaceutically purposes, the obtained suspension could be used or further processed without the need for drying.

After collection, the obtained particles of the glycopyrronium salt are substantially crystalline. Preferably, said particles should have a crystallinity equal to or higher than 90% or, more preferably, equal to or higher than 95%, more preferably higher than 98% as determined on the whole powder according to methods known to the skilled person.

During particle size reduction of active pharmaceutical ingredients by mechanical attrition, much of the mechanical energy generated is transferred to the processed solid and is stored in the form of lattice defects. In this way the processed solid system gains an activated stated and therefore, is described as being "mechanically activated." Said process may induce a structural disorder that is not uniformly distributed throughout the powder mass, and is focused at surfaces that have been exposed to the processing stress resulting in the generation of disorder or amorphous regions on the particle surfaces. Consequently, it may affect the physical properties of the materials during storage, in turn causing changes in the flow properties and fine drug particle delivery upon aerosolization.

An approach to measure the force balance and stability of the active ingredient particles is by cohesive-adhesive balance (CAB) analysis. Said approach measures the forces of interaction of the active ingredient particles, which are mounted on AFM probes, on well-defined crystalline surfaces of carrier substrates, according to the method disclosed in Begat P., et al., *Pharm. Res.*, vol. 21(9), pp. 1591-1597 (2004), which is incorporated herein by reference in its entirety. A CAB plot generated from the interaction number of probes enables direct quantification of the characteristic cohesive/adhesive ratio of the active ingredient particles within a carrier-based formulation.

Advantageously, the particles of the glycopyrronium salt obtainable by the process of the present invention have a cohesive-adhesive balance (CAB) value of 0.5 to 1.5, more advantageously of 0.7 to 1.3, preferably of 0.8 to 1.2.

At least 90% of the obtained particles of the glycopyrronium salt [d(v0.9)] should have a diameter of less than 10 microns, advantageously of less than 9 microns, preferably of less than 8 microns, more preferably of less than 7 microns. In a preferred embodiment, at least 90% of the obtained particles have a diameter equal to or lower than 6 microns. Preferably the d(v0.5) is from 1 to 4.5 microns, preferably from 2 to 4 micros.

In this context, the particle size is determined as volume diameter according to methods known to the skilled person such as laser diffraction based on the use of suitable apparatus such as Malvern apparatus.

In general, drug particles of this size are suitable for administration by inhalation. In fact particles having a particle size greater than about 10 microns are likely to impact the walls of the throat and generally do not reach the lung.

Advantageously, the specific surface area of the obtained particles upon drying and sieving, is from to 8 $m^2/g$, advantageously from to 7 $m^2/g$, preferably from 3 to 6 $m^2/g$. The Specific Surface Area is determined by Brunauer-Emmett-Teller (BET) nitrogen adsorption method according to a procedure known in the art.

Advantageously, the micronized drug particles obtainable with the process of the invention could be physically and chemically stable for at least a month at ambient conditions (22±2° C. and 60% relative humidity). Preferably, said micronized particles could be stable for at least 6 months at the same ambient conditions. More preferably, said particles could be stable for at least 1 month at 40° C. and 75% relative humidity, even more preferably for 6 months.

The physical stability can be measured by using a Sympatec Dry Dispersion Size Analyser, while the chemical stability can be determined according to method known to the skilled person such as HPLC.

Alternatively, the physical stability may be measured using the specific surface area of the drug particles analysed by adsorption analysis, BET surface measurement, according to a method known to the skilled person.

In this case, there should not be a significant decrease in specific surface area of the drug particles after 1 month, preferably after 6 months, upon storage at ambient conditions (22±2° C. and 60% relative humidity). Preferably, there could be a decrease of less than 1 $m^2/g$, more preferably less than 0.5 $m^2/g$ and even more preferably less than 0.2 $m^2/g$ in specific surface area of the drug particles after 1 month, preferably after 6 months upon storage at the same ambient conditions.

Particles of glycopyrronium salts that have been obtained in accordance with the process of the present invention have a reduced tendency to agglomerate and thus provide a substantially stable solid bulk drug that facilitates further processing, i.e. admixing with propellants or carrier particles, thus providing formulations having a good homogeneity.

Therefore, the present invention also encompasses inhalable pressurized formulations in form of suspension of the afore-mentioned micronized particles in a pressure-liquefied propellant, preferably a hydrofluoroalkane (HFA) propellant selected from the group of 1,1,1,2-tetrafluoroethane (HFA134a), 1,1,1,2,3,3,3-heptafluoro-propane (HFA227), and any mixtures thereof.

Furthermore, the present invention encompasses inhalable dry powder formulations comprising the afore-mentioned micronized particles in admixture with particles of a physiologically acceptable pharmacologically-inert solid carrier, such as lactose, preferably alpha-lactose monohydrate and optionally of further additives such as magnesium stearate.

Said formulations can be administered by suitable devices such as pressurized metered dose inhalers (pMDIs) or dry powder inhalers (DPIs).

The micronized particles obtainable with the process of the present invention may be used for prophylactic purposes or for symptomatic relief for a wide range of conditions including: respiratory disorders such as chronic obstructive pulmonary disease (COPD) and asthma of all types. Other respiratory disorders for which the product of the present invention may be beneficial are those characterized by obstruction of the peripheral airways as a result of inflammation and presence of mucus, such as chronic obstructive bronchiolitis, chronic bronchitis, emphysema, acute lung injury (ALI), cystic fibrosis, rhinitis, and adult or respiratory distress syndrome (ARDS).

In addition, said particles may be useful in treating smooth muscle disorders such as urinary incontinence and irritable bowel syndrome; skin diseases such as psoriasis; hyperhydrosis and sialorrhea; and gastrointestinal ulcers.

Other features of the invention will become apparent in the course of the following descriptions of exemplary embodiments which are given for illustration of the invention and are not intended to be limiting thereof.

EXAMPLES

Example 1

Preparation of a Micronised Powder of Rac-Glycopyrronium Bromide Using Wet Bead Milling in 2H,3H-Decafluoropentane Coarse rac-glycopyrronium bromide was suspended in 2H,3H-decafluoropentane as anti-solvent (100:1 ratio w/v) into which zirconia grinding media was added to give a drug/milling media ratio of 1:40 w/w. The resulting suspension was then loaded into the planetary mill apparatus disclosed in WO 2007/020407, which is incorporated herein by reference in its entirety, and the sample processed under ambient temperature and pressures of 1 bar (100 kPa), using a rotor speed of 200 rpm and processing time of 60 minutes. As post processing, the resulting suspension was passed through a nylon filter to remove the coarse grinding media, and the resulting liquid dispensed onto a metal tray to produce a fine bed. The solvent was then left to evaporate under ambient temperature for 4 to 6 hours to leave a fine, flowable powder which was subsequently passed through a 100 μm mesh to disperse the coarse aggregates. The resulting material was then tested for physical form integrity using the analytical tests described below.

Example 2

Analysis of Rac-Glycopyrronium Bromide Powder Material

Examination by Scanning Electron Microscopy (SEM) showed the coarse rac-glycopyrronium bromide as irregular crystals of about 30 to 100 μm. Product quality and particle size changes radically during the homogenization step with morphology of glycopyrrolate changing from large, irregular size crystallites to more compact, platelet-like particles with an average size markedly below 5 μm. After micronization and drying, particle size analysis by Laser light diffraction again shows that that the micronization process was successful, with a d(v0.5) of 1.85 μm, determined by using the Sympatec Dry Dispersion Size Analyser.

Specific surface area (SSA) of the dried and sieved particles, analyzed by BET nitrogen adsorption method, was determined to be of about 4.3 m$^2$/g. Analyzing the final product using X-ray powder diffraction analysis (XPRD) and DSC showed no change in degree of crystallinity or polymorphic form compared to the initial coarse drug.

The results in terms particle size distribution (PSD), XPRD, and SSA, upon storage at ambient conditions (22±2° C. and 60% relative humidity) are reported in Table 1 (w=week; m=months).

TABLE 1

| Time | PSD | | | XRD | BET SSA (m$^2$/g) |
| --- | --- | --- | --- | --- | --- |
|  | d(v0.1) | d(v0.5) | d(v0.9) |  |  |
| 0 | 0.71 | 1.85 | 4.77 | Crystalline | 4.326 |
| 1 W | 0.72 | 1.92 | 5.03 | — | 4.198 |
| 2 W | 0.72 | 1.88 | 4.95 | — | 4.210 |
| 4 W | 0.72 | 1.93 | 4.97 | Crystalline | 4.086 |
| 3 M | 0.75 | 2.07 | 5.26 |  | 4.00 |

In particular, the results indicate that, upon storage, the particle size does not significantly change and the variations maintain within the experimental error of the determination.

Example 3

Preparation of a Dry Powder Formulation Wherein the Active Ingredient is Rac-Glycopyrronium Bromide Alpha-lactose monohydrate SpheroLac 100 (Meggle) and magnesium stearate in the ratio of 98:2% by weight were co-milled in a jet mill apparatus (hereinafter the pre-blend). This pre-blend was then mixed with alpha-lactose monohydrate CapsuLac (212-355 micron) in a Turbula mixer for 4 hours at 32 rpm (hereinafter the Carrier). Micronized rac-glycopyrronium bromide as obtained in Example 1 was added to the Carrier and mixed in a Turbula mixer for 2 hours at 32 rpm to obtain a ratio of 12.5 μg of active to 10 mg of carrier (blend A).

A second formulation was prepared according to the same procedure by using micronized rac-glycopyrronium bromide after 3 months of storage at 22±2° C. and 60% relative humidity (blend B).

The formulations manufactured were assessed for satisfactory bulk powder content uniformity (RSD less than 5%).

An amount of powders for inhalation was loaded in the multi-dose dry powder inhaler (NEXThaler®-Chiesi Farmaceutici SpA, Italy). The aerodynamic assessment of particle size distribution was obtained by using a Next Generation Impactor (NGI) following the procedure detailed in the European Pharmacopeia (European Pharmacopoeia 7th Edition: 278-82, which is incorporated herein by reference in its entirety). Three consecutive doses were collected under an operating flow rate of 57 L/min. The required flow rate was obtained by adjusting the critical flow valve, ensuring that critical flow conditions were always maintained. After the required actuations powder deposited on the different stage of the impactor was recovered by using a 40:60 (v/v) water:methanol mixture and was then quantified by High Performance Liquid Chromatography (HPLC). Calculation of the aerodynamic deposition parameters, i.e. fine particle mass (FPM), fine particle fraction (FPF) and mass median aerodynamic diameter (MMAD) was performed by using CITDAS (Copley Inhaler Data Analysis Software).

The determination of delivered dose (DD) was obtained by collection of single actuations into dose unit sampling apparatus (European Pharmacopoeia 7th Edition: 3825-3829, which is incorporated herein by reference in its entirety) and using the same HPLC method used for the NGI analysis.

The results of blend A and B in terms of aerosol performance are reported in the Table 2.

TABLE 2

Aerosol Performance.

| Blend | Delivered Dose (μg) | Fine Particle Mass (μg) | Fine Particle Fraction (%) | MMAD (μm) |
|---|---|---|---|---|
| A | 9.9 | 7.0 | 61.3 | 1.84 |
| B | 11.6 | 6.5 | 55.9 | 1.59 |

The aerosol performance was re-assessed on blend A after storage at 22±2° C. and 60% relative humidity for 4.5 months. The data are summarized in the Table 3.

TABLE 3

Aerosol Performances of blend A after storage at 22 ± 2° C. and 60% relative humidity for 4.5 months.

| Blend | Delivered Dose (μg) | Fine Particle Dose (μg) | Fine Particle Fraction (%) | MMAD ((μm) |
|---|---|---|---|---|
| A | 11.6 | 6.3 | 54.7 | 1.61 |

The formulations obtained with rac-glycopyrronium bromide as obtained in Example 1 show consistency of delivered dose and very good aerosol performance as well with about 60% of FPF also after 3 months of the micronization process and after 4.5 months of the blend preparation.

Example 4

Preparation of a Micronised Powder of Rac-Glycopyrronium Bromide Using Wet Bead Milling in Dichloromethane Coarse rac-glycopyrronium bromide was suspended in dichloromethane as anti-solvent (100:1 ratio w/v) into which zirconia grinding media was added to give a drug/milling media ratio of 1:40 w/w. The resulting suspension was then loaded into the planetary mill apparatus disclosed in WO 2007/020407, which is incorporated herein by reference in its entirety, and the sample processed under ambient temperature and pressures of 1 bar (100 kPa) and processing time of 60 minutes. As post processing, the resulting suspension was passed through a nylon filter to remove the coarse grinding media and the resulting liquid dispensed onto a metal tray to produce a fine bed. The solvent was then left to evaporate under ambient temperature to leave a fine, flowable powder which was subsequently passed through a 100 μm mesh to disperse the coarse aggregates.

After micronization and drying, particle size analysis by Laser light diffraction shows that that the micronization process was successful, with a d(v0.5) of 2.06 μm, determined by using the Sympatec Dry Dispersion Size Analyser.

Upon analysis of the final product using DVS, no change in degree of crystallinity or polymorphic form was observed in comparison to the initial coarse drug.

The results in terms particle size distribution (PSD) are reported in Table 4.

TABLE 4

| | PSD | | |
|---|---|---|---|
| Time | d(v0.1) | d(v0.5) | d(v0.9) |
| 0 | 0.80 | 2.06 | 6.46 |

A formulation (blend C) was prepared according to the same procedure described in Eample 3. The results in terms of aerosol performance reported in the Table 5 show that consistency of delivered dose and very good aerosol performance (FPF 66%) are obtained also for the formulation wherein the active ingredient was suspended in dichloromethane as anti-solvent.

TABLE 5

Aerosol Performances.

| Blend | Delivered Dose (μg) | Fine Particle Mass (μg) | Fine Particle Fraction (%) | MMAD (μm) |
|---|---|---|---|---|
| C | 9.87 | 6.5 | 66.0 | 1.63 |

Example 5

Preparation of a Micronised Powder of Rac-Glycopyrronium Bromide Using Wet Bead Milling in Perfluoroheptane Coarse rac-glycopyrronium bromide was suspended in a mixture of isomers of perfluoroheptane using the same procedure disclosed in Examples 1 and 4. After 45 minutes of processing time, the particle size of the micronized material was measured using the Sympatec Dry Dispersion Size Analyser. The results in terms particle size distribution (PSD) are reported in Table 6.

TABLE 6

| | PSD | | |
|---|---|---|---|
| Time | d(v0.1) | d(v0.5) | d(v0.9) |
| 0 | 0.66 | 1.70 | 4.31 |

A formulation (blend D) was prepared according to the same procedure reported in Example 3. The aerosol performance is summarized in Table 7.

TABLE 7

Aerosol Performance.

| Blend | Delivered Dose (μg) | Fine Particle Mass (μg) | Fine Particle Fraction (%) | MMAD (μm) |
|---|---|---|---|---|
| D | 9.8 | 5.7 | 57.2 | 1.58 |

Particle size reduction of glycopyrrolate using perfluoroheptane as anti-solvent demonstrated successful particle size reduction with physical stable produced particles.

Comparative Example. Preparation of a micronised powder of rac-glycopyrronium bromide using wet bead milling in acetone.

Coarse rac-glycopyrronium bromide was suspended in acetone into which zirconia grinding media was added to give a drug/milling media ratio of 1:40 w/w. The vessel was sealed and the suspension homogenized into the planetary mill apparatus disclosed in WO 2007/020407, which is incorporated herein by reference in its entirety, at a disc speed of 200 rpm for 60 minutes at ambient temperature and pressure. After 60 minutes, the resulting drug suspension is separated from the milling media by filtering through a nylon mesh and the resulting drug suspension loaded into a drying tray. The solvent was then evaporated at 25° C. under low vacuum until dry to yield a white to off-white solid cake that could not be re-dispersed under mechanical agitation and as such could not be further processed.

Thus, processing in water miscible anti-solvents previously employed in particle size reduction by high pressure homogenization results in irreversible particle agglomeration during drying at low temperature.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for preparing micronized particles of a pharmaceutically acceptable salt of glycopyrronium, said process comprising:

feeding an anti-solvent, which is a water-immiscible hydrocarbon or derivative thereof which is liquid at room temperature and pressure, and has a dielectric constant lower than 15 and a density of 1.3 to 2 $g/cm^3$ to a micronization chamber of a wet milling apparatus, which optionally contains a grinding medium;

suspending particles of the glycopyrronium salt in said anti-solvent, to obtain suspended particles;

micronizing said suspended particles at a pressure equal to or lower than 200 kPa, to obtain micronized particle; and optionally, drying said micronized particles, whereby at least 90% of said micronized particles have a diameter of less than 10 microns.

2. A process according to claim 1, further comprising collecting said micronized particles.

3. A process according to claim 1, wherein said pharmaceutically acceptable salt is an organic salt.

4. A process according to claim 1, wherein said pharmaceutically acceptable salt is an inorganic salt.

5. A process according to claim 4, wherein said inorganic salt is selected from the group consisting of fluoride chloride, bromide, iodide, phosphate, nitrate, and sulfate.

6. A process according to claim 5, wherein salt of glycopyrronium is the bromide salt.

7. A process according to claim 6, wherein glycopyrronium is the racemic mixture of the enantiomers (3S,2'R), (3R,2'S).

8. A process according to claim 1, wherein said anti-solvent is an n-alkane or an haloalkane and is a liquid at room temperature and pressure.

9. A process according claim 8, wherein said anti-solvent is n-heptane.

10. A process according to claim 8, wherein said anti-solvent is a fluoroalkane or a hydrofluoroalkane.

11. A process according claim 10, wherein sid anti-solvent is selected from the group consisting of perfluorodecane, decafluoropentane, and 2H,3H-decafluoropentane.

12. A process according to claim 1, further comprising washing said micronized particles with a second anti-solvent.

* * * * *